United States Patent [19]
Hounsfield

[11] 4,002,911
[45] Jan. 11, 1977

[54] DATA ACQUISITION IN TOMOGRAPHY

[75] Inventor: Godfrey Newbold Hounsfield, Newark, England

[73] Assignee: EMI Limited, Hayes, England

[22] Filed: Aug. 27, 1975

[21] Appl. No.: 608,204

Related U.S. Application Data

[63] Continuation of Ser. No. 471,658, May 20, 1974, abandoned.

[52] U.S. Cl. .......................... 250/360; 250/445 T
[51] Int. Cl.² ................. G01N 21/34; G01N 23/00
[58] Field of Search .............. 250/360, 445 T, 312, 250/46 D, 320–323, 492

[56] References Cited
UNITED STATES PATENTS

| 3,748,470 | 7/1973 | Barrett | 250/320 |
|---|---|---|---|
| 3,755,672 | 8/1973 | Edholm | 250/322 |

Primary Examiner—Harold A. Dixon
Attorney, Agent, or Firm—Fleit & Jacobson

[57] ABSTRACT

Apparatus is so constructed as to employ a sampling beam of radiation of a form which at least approximates to a sinusoidal distribution of intensity between the extremities of its skirts, and is such that the range of sinusoidal variation has an extent of approximately four sampling intervals, whereby the sampling beams have themselves the effect of band limiting the required data to a spatial frequency of approximately half the sampling frequency.

5 Claims, 8 Drawing Figures

DATA ACQUISITION IN TOMOGRAPHY

This is a continuation application of Ser. No. 471,658, filed May 20, 1974, now abandoned.

This invention relates to apparatus for examining a body by means of radiation, such as X or γ radiation.

In our U.S. Pat. Spec. No. 3,778,614 there is described apparatus for carrying out such examinations in which a source of radiation and detecting means are mounted to face each other across an aperture in which the body to be examined can be located, the apparatus being intended for examination of part of the human body. The detecting means is arranged to detect a narror beam of radiation transmitted from the source through the body. Locating means are provided for locating the part of the body to be examined in the aperture and it may be adapted to receive, for example, the head or some other part of the human body. In order to carry out the examination, scanning means are provided for producing inter-related orbital and lateral scanning movements of the source and the detecting means in a plane normal to the axis of the aperture so that the beam of radiation to which the detecting means is sensitive scans the body to be examined in a direction substantially normal to its length due to the lateral scanning movements, and with many different orientations resulting from the orbital scanning movement. During each lateral scan, a set of output signals is derived from the detecting means representing the transmission or the absorption of the body, with respect to the radiation, along a set of closely spaced parallel beam paths in the said plane.

Since a lateral scan occurs for each of a series of successive increments of the orbital scanning movement successive sets of signals are derived corresponding to sets of closely spaced paths orientated at different angles or mean angles. From the many sets of output signals, a representation of a variable transmission or absorption in the plane section of the body under examination can be reconstructed.

Each set of output signals constitutes samples of the data, an image of which is to be reconstructed.

It is known that a sampled function which at all points is finite, and continuous in relation to its variable, can in principle be reconstructed free of error from a large number of samples of the function taken at uniform intervals in the variable, if these intervals are sufficiently small, that is to say if the sampling occurs at a sufficiently high rate. This rate must be a least twice the repetition frequency of the Fourier component of the sampled function which is of the highest order: otherwise the function cannot be regained without error.

In the use of apparatus as envisaged there are circumstances, which can arise for example when the apparatus is directed to the examination of the human body for the purposes of medical diagnosis, when an object present in the field of examination, such as a bone structure, can present spatial rates of change that call for undesirable or impracticably high rates of sampling if the requirement stated is to be met.

If the requirement is not met then the iterative method of reconstruction of the absorption pattern, as set out in said specification, from the sampled data, tends to give rise to spurious patterns spread over the reconstructed image. Such superposed patterns tend also to occur if the reconstruction is by convolution processing. An object of the invention is to surmount or reduce this difficulty.

According to one form of the invention the apparatus is so constructed as to employ a sampling beam of radiation of a form which at least approximates to a sinusoidal distribution of intensity between the extremities of its skirts, and is such that the range of sinusidal variation has an extent of approximately four sampling intervals, whereby the sampling beams have themselves the effect of band limiting the required data to a spatial frequency of approximately half the sampling frequency.

Apparatus according to the invention may operate so that the sets of signals derived from the differently angularly disposed sets of beam paths as envisaged in the aforesaid specification, are obtained in 180° of the orbital scanning movement. Alternatively the signal derivation may be completed in two successive such movements, and other modes of operation are possible within the scope of the invention.

In order that the invention may be more clearly understood and readily carried into effect it will now be described by way of example with reference to the accompanying drawings in which:

FIG. 1 shows the structural character of means for the acquisition, in apparatus of the kind contemplated, of beam absorption data, this means being of a nature suitable for use in accordance with the invention and for the examination of a patient for the purposes of medical diagnosis;

FIG. 2 sets out in broad outline a form of circuit by which in such apparatus the data so acquired may be initially integrated and processed to render it appropriate for subsequent image reconstruction processing;

Figure 2:
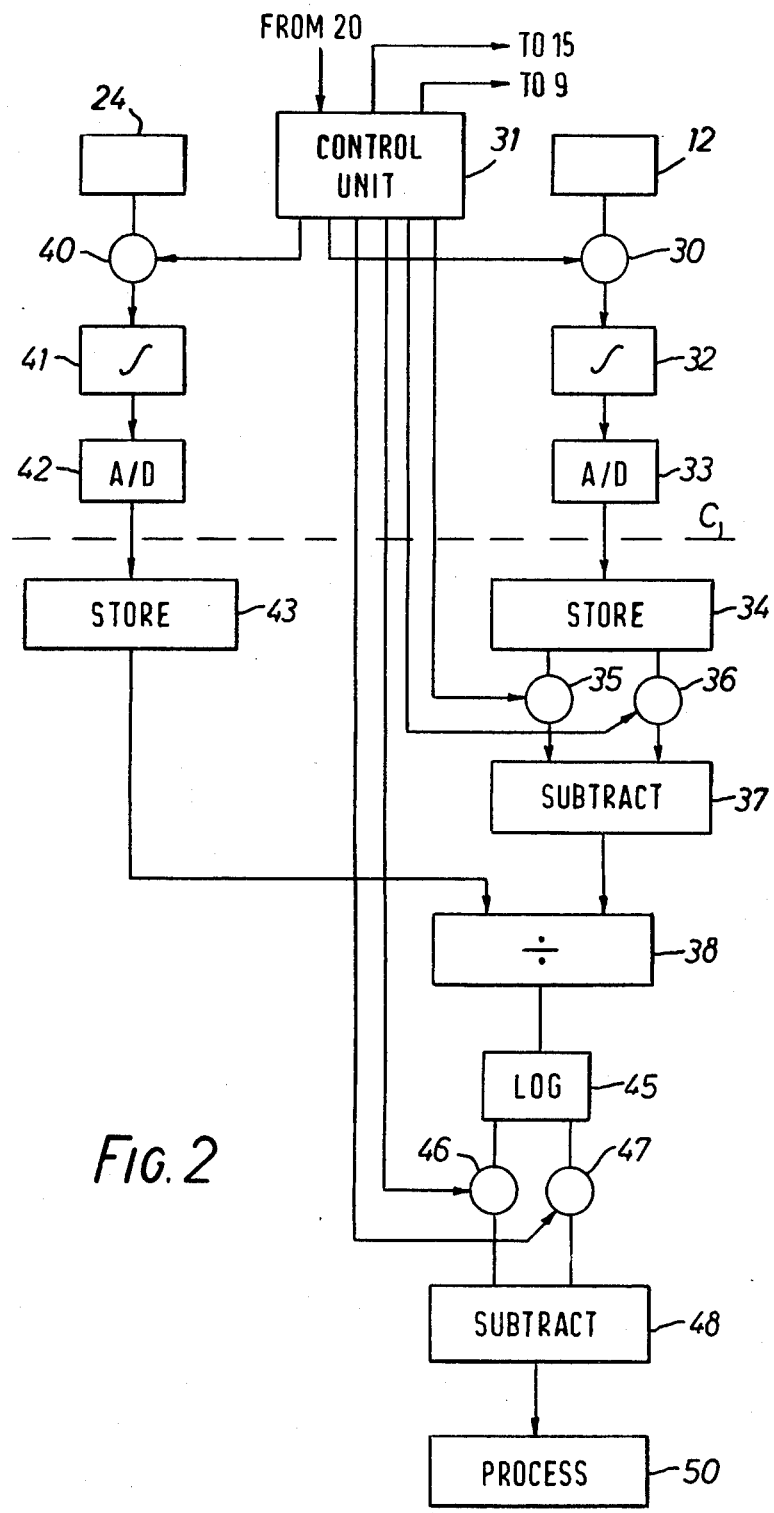
Figure 5A:
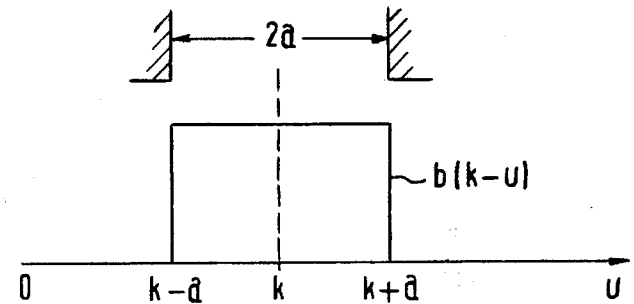
Figure 5B:
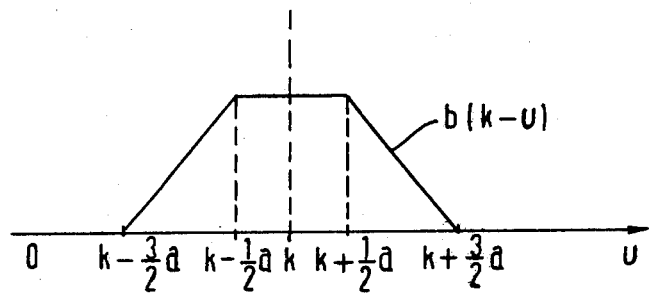
Figure 5C:
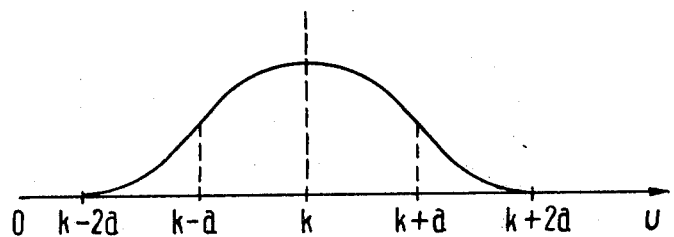
Figure 6:
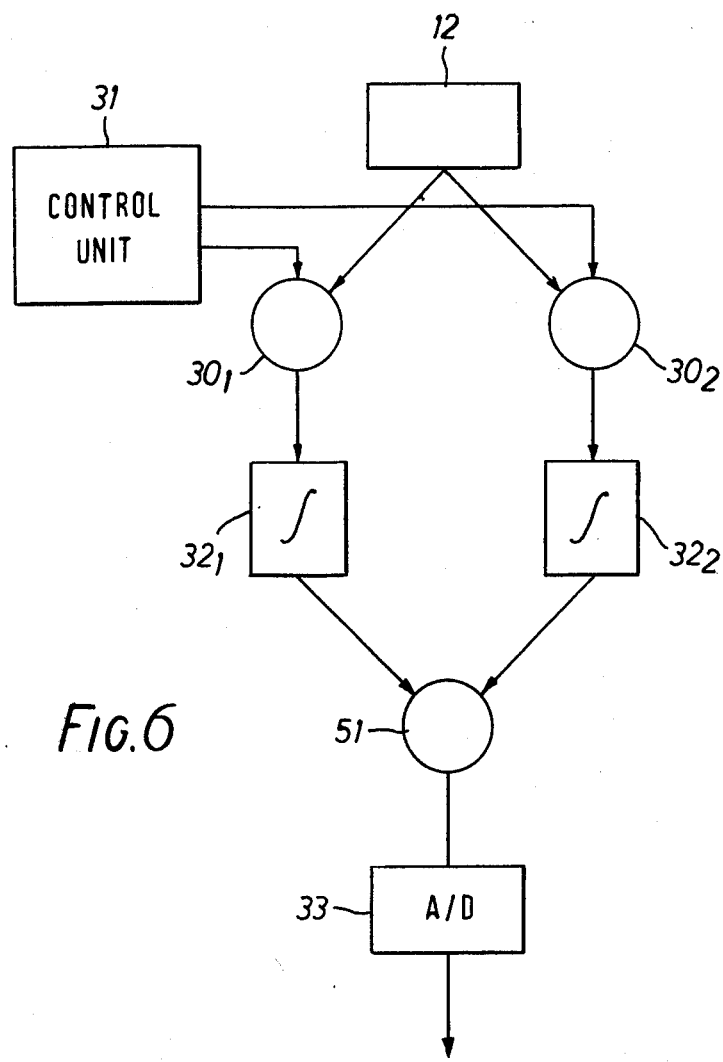

FIG. 5(a), 5(b) 5(c) show different forms of effective distribution of radiation intensity of sampling beams in the direction of the scanning movement; and FIG. 6 relates to the feature of integration of the circuit set out in FIG. 2 showing a particular form this feature may take.

Figure 1:
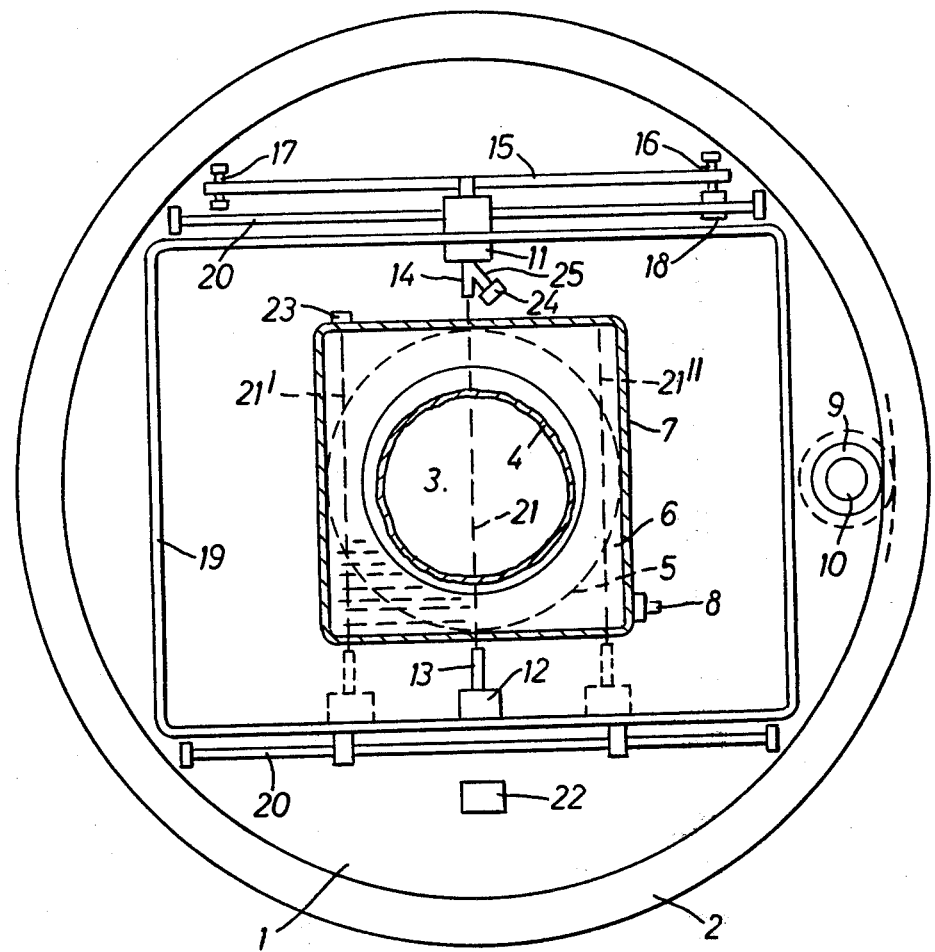

Referring to the drawings, the arrangement of FIG. 1 is in a form adapted to the examination of the head of the patient and comprises a rotary member 1 which is rotatable inside a fixed casing 2 forming part of the main frame of the general apparatus. The rotary member 1 has a central aperture 3 in which the head of the patient to be examined can be inserted. The central aperture is closed in a water-tight manner by a pouched cover 4 of flexible material which is secured to a sealing flange 5. This flange is held in sealing but rotatable, relationship with the remote face of the member 1. The pouch is shown in section in FIG. 1. The head of the patient is inserted through the aperture 3 into the pouch of the cover 4, and an additional head rest, not shown, may be provided to support the head in the pouch. A suitable chair or bed is provided to support the patient during the examination. When the head is inserted through the aperture 3 into the pouch 4 it projects into a water reservoir 6 having side walls 7, the pouch separating the head from the water. The reservoir is closed at the front by the member 1 and cover 4, at the side by the walls 7 which are made of plastic, and at the rear by a base wall, not shown. The walls 7 and the base wall rotate with the member 1, whereas the cover 4 with its flange 5 remain stationary, the flange being secured to the frame of the apparatus. A pipe 8 is connected to a pump for feeding water to and from the reservoir and after the patient's head has been inserted in the pouch, water is pumped into the reservoir 6 so as to expel the air from between the pouch and the patient's head.

A toothed-gear wheel 9, driven by a motor 1 has provided for driving the rotatable member 1 so as to produce orbital scanning of the member 1 about its axis, which is also the axis of the aperture 3. The gearwheel 9 engages teeth formed around the inner periphery of the casing member 2. The rotatable member carries a source 11 of penetrating radiation, an X-ray generating tube in this example, and facing the source 11, on the other side of the aperture 3 there is provided an X-ray detector 12. The detector 12, which comprises a scintillating crystal and a photomultiplier, has a collimator 13. The source of the radiation 11 is arranged to be an effective point source and it has a collimator 14, the collimators 13 and 14 confining the radiation reaching the detector 12 to a single narrow beam 21 lying in a plane section normal to the axis of the rotary member 1. The plane lies within the reservoir 6.

The source 11 is secured to a toothed belt 15 driven by a toothed drive shaft 16 journalled in the rotatable member 1, the belt being extended between the shaft 16 and the second shaft 17 also journalled in the member 1. The shaft 16 is driven by a reversible motor 18, the controls of which are interlocked with those of the motor 10. Since the source 11 is massive, a counter balance weight, not shown, is provided secured to the other run of the belt so as to move reciprocally with the source. In operation of the apparatus, the source 11 and the collimator 14 are caused by the motor 18 to execute to and from lateral scanning movements in the aforementioned plane normal to the axis of the rotary member 1. The detector 12 with its collimator 13 are coupled to the source 11 by a yoke 19 so that they execute the same lateral scanning movements. Guides 20 are provided to support the source and the yoke during the lateral scanning. Output signals are derived from the detector 12 during each lateral scan and those signals represent the transmission or absorption of the beam 21 along a sampling set of closely spaced parallel beam paths in the planar section under examination.

The interlock beween the motors 10 and 18 is such that following each lateral scan, in one or other direction, an increment of orbital movement of say 1° is imparted to the rotary member 1 by the motor 10. Thereafter another lateral scan occurs under the control of the motor 18 but this tine in the reverse direction to the preceding lateral scan. A further set of output signals representing the transmission of the beam 21 along a further set of closely spaced parallel beam paths is derived, this set of beam paths being orientated at 1° relative to the preceding set. A photocell device, represented diagrammatically by the block 22, and co-operating with a graticule, not shown, coupled to the yoke 19, is provided to monitor the lateral scanning displacements and determine the timing of the output signals. The alternate orbital and lateral scanning movements are continued until a total orbital movement of 180° has been completed.

As indicated in FIG. 1, the reservoir 6 has a lateral extent substantially equal to that of the lateral scan, the extremities of which are indicated by the dotted beams 21' and 21''. It projects to either side of the aperture 3 so that at the beginning of each lateral scan the beam 21 is for a time traversing a known path length through the water in the reservoir. The reservoir, when filled with water, thus provides a reference attenuator so positioned relative to said locating means as to provide a known attenuation of the beam 21 at the beginning of each lateral scan before the beam passes to the body to be examined. As will appear subsequently a reference signal is derived from the detecting means while the beam is intercepted by the water reservoir and this reference signal is utilised for modifying output signals derived when the beam is intercepted by the body to be examined. As the walls of the reservoir, other than the cover 4, rotate with the member 1, the path of the beam through the reference attenuator provided by the side portions of the reservoir 6 is substantially the same for every lateral scan regardless of the angular orientation. There is also provided mounted on the member 1 a block of lead 23 which is located at one extremity of the lateral scans carried out by the source 11 and detector 12. The lead block 23 provides substantially complete absorption of the X-radiation and the output signal from the detector 12 when the beam is intercepted by the lead provides a second reference signal which is utilised to modify the signals derived from the detector not only when the beam 21 is intercepted by the body to be examined, but also when it is intercepted by the parts of the reservoir which act as reference attenuators. It is to be noted that the reservoir 6 provides attenuation of the beam 21 throughout the lateral scanning movements, but the attenuation is reduced in the regions where the beam is liable to be intercepted by the body to be examined. The attenuation or absorption coefficient of water is such that the total absorption of the beam 21 is approximately the same throughout each lateral scan, when the body to be examined is positioned in the pouch (except of course when the beam is intercepted by the lead block 23). In the circuit for processing the output signals of the detector 12, and as will be described in more detail with reference to FIG. 2, the logarithm of the reference signal derived when the beam suffers the known attenuation at the beginning of each lateal scan is subtracted from the logarithm of the other output signals, and the resultant output signals represent substantially only differences in the attenuation of the beam within the body examined from that of transmission through water.

A reference detector 24 is mounted cloe to the X-ray source 11 so that it receives radiation directly from the source via a collimator 25. The detector 24 is provided to monitor the energy of the X-rays.

The circuit set out in FIG. 2 commences with the detectors 12 and 24 of the mechanism that has been described with reference to FIG. 1. The output signals of the detector 12 are applied to a gate 30 which is opened at predetermined times by pulses from a master control circuit 31. This master control circuit receives input signals from the photocell device 22 and feeds out suitable control signals not only to the gate 30 but also to the motor 10 and to the reversing motor 17. The pulses which it feeds to the gate 30 are produced at times determined by the aforesaid graticule so as to derive from the detector 12 a succession of output signals corresponding to the transmission of the beam 21 through a sampling set of parallel beam paths, as already indicated. The orientation for the set of paths is determined by the angular position of the rotation member 1. During each sampling interval the output of the detector 12 is integrated in an integrator 32 and then converted to digital code form in an analogue-to-digital converter 33. Each signal so generated is stored in its digital form in a store 34. The X-ray beam 21 is intercepted by the lead block 23 once in two lateral scans and therefore the corresponding output signal from the detector 12 is stored for the duration of two traverses. The signals of a particular parallel set of paths in the store 34 include those obtained when the X-ray beam 21 is known to pass through the reference paths in the reservoir 6 and those obtained when passing through the body under examination. Gate 35 is provided for selecting the output signal derived from the detector at the time when the beam 21 is substantially interrupted by the lead block 23. Another gate 36 is provided for selecting the signals derived at other traversal times. The selection is controlled by further pulses derived from the master control circuit 31 and in such a way that the reference signal representing the virtually complete attenuation introduced by the lead is subtracted from each other signal of a sampling set, so that after the subtraction the resulting signals represent the transmission or absorption of the beam 21 within the examined body related to the absorption of lead as a datum. In this way the effect of 'after glow' in the detector 12 is largely removed. The resulting signals are passed into dividing circuit 38.

The reference detector 24 previously referred to has an output gate 40 which is controlled by pulses also derived from the master control circuit 31 and coincident with the pulses applied to the gate 30. Signals passing through the gate 40 are integrated in an integrated 41 and converted to digital form in a converter 42, these components 41 and 42 corresponding to the integrator 32 and converter 33. The digitised signals from the detector 24 are then passed to a store 43 and applied thence to the aforesaid dividing circuit 38.

In the dividing circuit each signal from the detector 12 is divided by the corresponding signal from the store 43 to compensate for variations in energy of the source 11. The signals so compensated are passed to a log converting circuit 45 which translates each signal from the detector 12, referenced on lead as the datum as explained, into its logarithm and holds them in this form. These signals are applied to two gates 46 and 47 which are controlled by pulses from the master control circuit 31. The gate 46 is opened at times corresponding to those when the X-ray beam 21, during any particular traverse, is passing through the region in which the body to be examined may be located, while the gate 47 is opened at other times corresponding to when the beam 21 is passing through the reference paths in the water and is therefore subjected to a known attenuation. The signals from the gate 47 may therefore be termed reference signals, those from the gate 46 being distinguished as output signals. The reference signal moreover is read out repeatedly to coincide with each output signal of a particular scan and it is subtracted from these output signals so that the output signals then represent the ratio of the attenuation of the beam 21 to the known attenuation produced by the water in the reservoir. Any spurious variations in the output signals, due to rapid drift on the sensitivity of the detector 12 are thus substantially compensated. The output signals after these modifications are fed to the signal processor 50 to participate along with the signals of all the other sets in the image reconstruction of the distribution of absorption of the exploring radiation in the section of the body under examination. This reconstruction may be achieved as described in our aforesaid patent specification, or by any other suitable method, for example by convolution. Of the components represented in FIG. 2, those located below the dotted line 'C' may take the form of a digital computer which is appropriately programmed and which feeds its output to a suitable picture reconstructing device.

Many variations may be made in the form of the apparatus. For example, the attenuator formed by the reservoir of water may be replaced by an attenuator made of solid material such as plastic, suitably shaped to provide an equivalent effect to that produced by the water reservoir. In this case a locating collar may be provided for the body to be examined and a separate water jacket disposed between the collar and the body located in the collar. To further improve the compensation for drift in the detector 12, the modification effected by the circuit 48 may be arranged to depend on the interpolation of successive reference signals from the gate 47. Several detectors such as 12, with appropriate collimators, may be provided to receive several beams of radiation from the source 11. In this case the said beams may be inclined at small angles to each other or may merge into a single fan beam. If the angle subtended by the fan beam is sufficient to include the body to be examined lateral scanning may be unnecessary. The total orbital scanning movement may moreover differ from 180°. There may, moreover, be two or more beams such as 21, one behind the other, so that two or more adjacent planes may be examined simultaneously.

Although as described the lateral scanning movement is continuous in the course of acquisition of the successive beam data samples of a set at the angular disposition concerned, the lateral scanning motion may be discontinuous so that there is no movement during datum acquisition as such.

Figure 3:
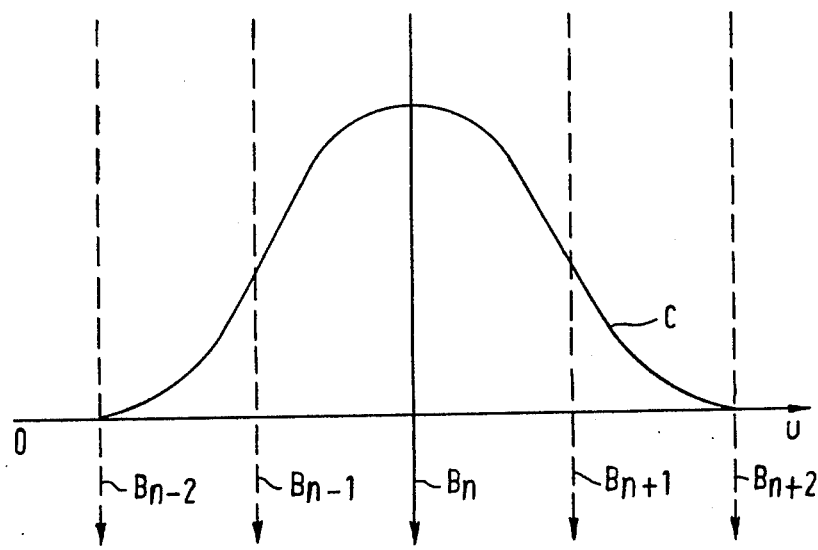
FIG. 3 illustrates the form of effective distribution of intensity, in the direction of the lateral scanning motion, of the sampling beam of radiation as used in accordance with the invention.

In FIG. 3 the curve C shows graphically a preferred form of effective distribution of radiation intensity across the sampling beam in the direction of lateral scanning. This direction is indicated in the figure by the axis Ou, which axis is that of the angular disposition of the particular sampling set concerned. It is assumed that the beam is located normally to the axis Ou and with its centre line along the path $B_n$. This path is taken to be one of the sampling positions of the set, $B_{n+1}$ and $B_{n-1}$ in broken line representing immediately adjacent positions in the sampling sequence, with $B_{n+2}$ and $B_{n-2}$ likewise representing next immediately adjacent positions. The intervals between such sampling paths are the same and equal to what is termed the sampling interval. The ordinate of the curve C at any point along the axis Ou represents the effective radiation intensity of the beam at that point. It will be seen that the curve extends from skirt extremity to skirt extremity over the extent of four sampling intervals. If $x$ represents distance along the Ou axis from the location of the path $B_n$, then as a function of $x$ the ordinate of the curve C is proportional sensibly to $$\tfrac{1}{2} + \tfrac{1}{2} |\cos| \pi x/2a,$$

in which $a$ represents the sampling interval.

In the circumstance that the scanning motion along the axis Ou is discontinuous the scanning beam remains static in each of the sampling positions, such as $B_n$, for a brief period during which the relevant absorption datum is acquired by the integration process referred to. Moreover the curve C should then represent the physical distribution of radiation intensity across the beam in the direction Ou. In practice it is a simpler matter to maintain the scanning as a continuous uniform motion, the integration process then extending over a range of beam positions. In this circumstance the form of the curve C is not that of the physical distribution of radiation intensity across the beam, but rather this distribution as modified effectively by the continuous scanning movement. The physical distribution is made more spread by the movement, and such an effect is commonly referred to as 'aperture effect'.

It is found that where the cross sectional shape of the aperture in the collimators 13 and 14 is made such as to provide at least approximately a beam intensity distribution such as indicated in FIG. 3, substantially improved image reconstruction can be obtained compared with other more sharply defined beam intensity distributions, such as for example a beam of which the spread is only $2a$. It is believed that this improvement can be explained as follows, though the invention is not dependent on the accuracy or completeness of the explanation.

Whether the curve C represents effectively the beam radiation distribution either because it represents the physical distribution of radiation in the circumstance of discontinuous motion scanning, or through aperture effect in the circumstance of continuous motion scanning, it gives rise to a sample of the absorption data proportional to $$\int_{-\infty}^{+\infty} f(u)b(k-u)du ,$$

in which $f(u)$ represents the line integral of absorption of the radiation along a path parallel to the path $B_n$ and intercepting the Ou axis at the coordinate distance $u$ along the axis, and $b$ is a function representing the form of the curve C so that ps
$b(x) = \frac{1}{2} + \frac{1}{2} \cos\pi x/2a$ The parameter $k$ in the instance when the sampling beam centre line is coincident with the path $B_n$ is the value of the coordinate distance $u$ at the point where $B_n$ intersects the Ou axis. The sample of the absorption data is a function of $k$ and so can be written $s(k)$.

By reason of the convolution form of the integral yielding the function $s(k)$ is one of many samples of the function $s(u)$, the spectrum modulus of which is equal to $$|F(i\omega)| \cdot |B(i\omega)|,$$

in which $F(i\omega)$ is the Fourier transform of $f(u)$ with respect to the angular frequency parameter $\omega$, while $B(i\omega)$ is likewise the Fourier transform of the beam acquision function $b(x)$.

As has been indicated earlier if the edge of a bone structure is present in the field of examination then the line integral function $f(u)$ may contain material components of frequency that exceed the half sampling frequency, and so obscure the reconstruction of the absorption pattern of the examination field by superposing thereon a spurious pattern. On the other hand if the spectrum $B(i\omega)$ is restricted so that for values of $\omega$ greater than the value corresponding to the half sampling frequency the value of $B(i\omega)$ is negligibly small, then the function $s(u)$ can contain no material components of frequency in excess of the half sampling rate. The absorption reconstruction pattern will then be free of the spurious kind of pattern mentioned.

Figure 4:
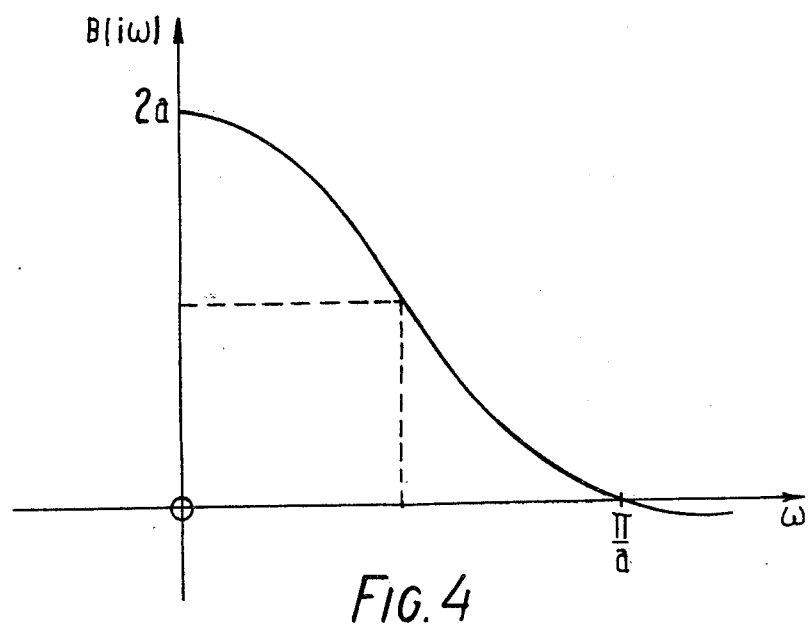
FIG. 4 is a theoretical diagram to aid in the understanding of the invention.

It may be shown that $$B(i\omega) = a \cdot \frac{\sin(2\omega a - \pi)}{2\omega a - \pi} + 2a \cdot \frac{\sin 2\omega a}{2\omega a} + a \cdot \frac{\sin(2\omega a + \pi)}{2\omega a + \pi}$$

and the plot of $B(i\omega)$ is graphed in FIG. 4. This plot indicates that $B(i\omega)$ has the value value $2a$ for $\omega=0$, the value $a$ for $\omega = \frac{1}{2}\pi/a$, and the value zero for $\omega = \pi/a$, passing smoothly through these values so as to be of small value only for values of $\omega$ in excess of $\pi/a$. The last value for $\omega$, namely $\pi/a$, corresponds to a spatial frequency of one half the sampling frequency. The function $b(x)$ thus ensures that the sampled function $s(u)$ contains substantially no components that will set up undesired spurious patterns in the absorption image reconstruction by reason of an otherwise insufficiently high sampling rate.

It will be realised that the beam data acquisition function $b(x)$ is a weighting function, since it weights the line integral contributions $f(u)du$ to the sampled datum $s(k)$. FIG. 5(a) gives an example of the situation when the sampling beam is of uniform intensity across the whole of its cross section in the direction of the scanning axis Ou. The figure shows the beam centred at the coordinate distance $k$ and extending in the Ou direction over the sampling range ($k$-a, $k$—a), that is to say over an interval equal to twice the sampling interval $a$. This assumes a collimator having an aperture of width $2a$ Clearly the beam would weight equally all values of the line integral function $f(u)$ in the range sampled, assuming the beam to be stationary whilst sampling occurs.

FIG. 5(b) shows the form of the weighting function $b(x)$, when, using the same sampling beam, such discontinuous motion scanning is replaced by continuous motion scanning, integration of the sampling detector output commencing when the beam centre line has just left the point of coordinate distance $k-\frac{1}{2}-\frac{1}{2}a$, and continuing until the beam centre line has just reached the point of coordinate distance $k+\frac{1}{2}a$. The weighting increases linearly with the uniform motion of the scan from the point $k-3/2a$ until the point of distance $k-\frac{1}{2}a$, when it remains uniform to the point of distance $k+\frac{1}{2}a$, when it remains uniform to the point of distance $k+\frac{1}{2}a$, decreasing linearly after this to the point $k+3/2a$. It will be understood that $k3/2a$ is the point which the trailing edge of the beam is just leaving when integration commences, whereas $k+3/2a$ is the point which the leading edge of the beam just reaches when integration ceases. The weighting function of FIG. 5(b) extends over three sampling intervals rather than the two intervals of the function of FIG. 5(a), showing how the continuous motion scanning effectively spreads or smears the physical distribution of the beam, and the term "beam" used herein and in the claims is intended to include the effective beam resulting from the integration and scanning parameters. With a beam the physical distribution of which is not sharply defined such as that presupposed in relation to FIG. 5(a), the weighting function shown in FIG. 5(b) can become transformed to one of the smooth shape of FIG. 5(c), and this may be of the symmetrical sinusoidal distribution earlier set out and extending over a range of four sampling intervals. Such a distribution may be contrived, if necessary by the appropriate use of absorbing material in the path of the beam to shape its distribution. This distribution as has been shown is suitable for the purposes of the invention. On the other hand these purposes may be sufficiently met by the use of the distribution of FIG. 5(b), or one which approximates more closely to this distribution than that of FIG. 5(c). In the practical form of the invention, illustrated in FIGS. 1 and 2, a distribution such as shown in FIG. 5(c) is obtained by using rectangular apertures of width 2a for the collimators 13 and 14, the smoothing-off illustrated in FIG. 5(c) resulting partly from the fact that the collimators are partially permeable to X-rays, and partially from the fact that the intensity of the X-rays from the tube 11 is not uniform over the width of the aperture as shown in FIG. 5(a).

It will be noted that whatever weighting distribution is employed, for continuous motion scanning the time of integration used for any one sample is the time it takes for the scanning beam to move over the distance of one sampling interval. The integrator circuit shown at 32 in the circuit diagram of FIG. 2 may thus in principle comprise a single integrator unit only. In practice in this event it would be necessary to arrange that the integrating period is slightly less than the period for the scanning beam to move over a sampling interval, so as to allow time for the integrated signal to be read out from the integrator and for the integrator to be reset so as to be ready to commence the integration over the next succeeding integration period. Alternatively the full period of the sampling interval may be used for integration and two integrator units may be employed, one being utilised for integration while the other is subject to read out and reset, and vice versa. The circuit scheme of FIG. 6 illustrates this alternative.

In this last figure the reference 12 again designates the sampling detector and the figure shows output signals from the detector fed to two gating circuits $30_1$ and $30_2$ respectively controlled by pulses from the control unit 31. Gated signals passed by these gates are applied respectively to integrator units $32_1$ and $32_2$. Each of these integrators integrates the signal input applied to it over the period of scanning traverse of one sampling interval, but the pulses controlling the gates provide for signal integration by the integrators in interleaved manner as already indicated, so that in periods intervening those of integrating the integrated signals can be transferred for subsequent processing and the integrators can be reset. Although not indicated, either in FIG. 6 or FIG. 2 the integrators are controlled, in particular in regard to reset, by the control circuit 31. As shown in FIG. 6 the signals read out from the integrators are applied to the OR gate 51 by which they are transferred in interleaved sequence to the analogue-to-digital converter 33.

While the invention is of application in those circumstances of reconstruction in which the iterative methods of the aforesaid specification are used, or the methods of convolution, it may also be employed in relation to any method of reconstruction in which the presence of high frequency components in the data sampled tends to give rise to the spread of spurious patterns of the kind mentioned.

What I claim is:
1. Apparatus for examining a body by means of penetrating radiation such as X—or Y—radiation, comprising,
   a. means for projecting the radiation through a planar section of the body,
   b. means for detecting the radiation emerging from the body to provide output signals, related to the detected radiation.
   c. means for scanning the means for projecting and means for detecting relative to the body so that said output signals relate to the transmission of the radiation along a plurality of sets of substantially parallel beam paths, for which the centre lines of adjacent beam paths of each such parallel set are separated by a distance $a$, to allow the reconstruction from the output signals of an image of the variable absorption or transmission coefficient of the section, and
   d. means for imposing an intensity distribution on the radiation across each of the beam paths in a direction at right angles to the beam path, said distribution being such as to limit the output signals to a spatial frequency band of which the practical upper limit is in the vicinity of or below the frequency $\frac{1}{2}a$.

2. Apparatus according to claim 1 wherein said means for imposing an intensity distribution includes a collimating means having an aperture of width approximately $2a$ and the scanning means arranged to scan the collimating means, together with the means for projecting and means for detecting, in relation to the body.

3. Apparatus according to claim 1 in which said means for imposing an intensity distribution is arranged such that the said distribution conforms to a substantially symmetrical sinusoidal curve having an extent of approximately $4a$ in a direction substantially at right angles to the beams.

4. Apparatus for examining a body by means of penetrating radiation such as X—or Y—radiation, comprising,
   a. means for projecting the radiation through a planar section of the body,
   b. means for detecting the radiation emerging from the body to provide output signals, related to the detected radiation and corresponding to the transmission of the radiation along at least one set of substantially parallel beam paths so that the centre lines of adjacent beam paths of the parallel set are separated by a distance $a$,
   c. means for orbiting the said means for projecting and means for detecting about an axis substantially perpendicular to the planar section to provide other sets at different angles so that an image of the variable absorption or transmission coefficient of the section can be reconstructed from the output signals and,
   d. means for imposing an intensity distribution on the radiation across each of the beam paths in a direction at right angles to the beam path, said distribution being such as to limit the output signals to a spatial frequency band of which the practical upper limit is in the vicinity of or below the frequency $\frac{1}{2}a$.

5. A method for examining a body by means of penetrating radiation such as X—or Y—radiation, comprising the steps of a. projecting radiation through the body along a plurality of coplanar sets of beam paths, the paths of a set being substantially parallel and the sets of paths being orientated at different angles in the plane of the sets,
b. deriving a plurality of output signals each corresponding to the radiation transmitted along a respective one of said paths,
c. establishing a spacing between the centre lines of adjacent paths in each set to be of a magnitude $a$,
d. establishing the width of each beam path to be substantially in excess of $2a$, and
e. establishing the distribution of the intensity of radiation across each of the beam paths in a direction at right angles to the path to be a maximum at substantially the centerline of each beam path, the distribution of intensity being related to the width of each beam path so as to limit the output signals to a spatial frequency band of which the practical upper limit does not exceed the frequency of approximately $\frac{1}{2}a$.

* * * * *

Disclaimer and Dedication

4,002,911.—*Godfrey Newbold Hounsfield*, Newark, England. DATA ACQUISITION IN TOMOGRAPHY. Patent dated Jan. 11, 1977. Disclaimer filed Apr. 28, 1978, by the assignee, *EMI Limited*.

Hereby disclaims and dedicates to the Public the entire remaining term of all claims of said patent.

[*Official Gazette June 13, 1978.*]